(12) United States Patent
Kopoian

(10) Patent No.: US 11,731,135 B2
(45) Date of Patent: Aug. 22, 2023

(54) NEEDLECUP

(71) Applicant: Marc Kopoian, Scottsdale, AZ (US)

(72) Inventor: Marc Kopoian, Scottsdale, AZ (US)

( * ) Notice: Subject to any disclaimer, the term of this patent is extended or adjusted under 35 U.S.C. 154(b) by 0 days.

(21) Appl. No.: 17/086,550

(22) Filed: Nov. 2, 2020

(65) Prior Publication Data

US 2022/0134345 A1 May 5, 2022

(51) Int. Cl.
*B01L 3/00* (2006.01)
*G01N 33/493* (2006.01)
*G01N 1/14* (2006.01)

(52) U.S. Cl.
CPC ............. *B01L 3/563* (2013.01); *G01N 1/14* (2013.01); *G01N 33/493* (2013.01); *B01L 2200/025* (2013.01); *B01L 2200/026* (2013.01); *B01L 2200/0689* (2013.01); *B01L 2200/082* (2013.01); *B01L 2200/085* (2013.01); *B01L 2200/141* (2013.01); *B01L 2300/042* (2013.01); *B01L 2300/046* (2013.01); *B01L 2300/0672* (2013.01); *B01L 2400/049* (2013.01)

(58) Field of Classification Search
CPC ........ A61B 5/150343; A61B 5/150351; A61B 5/150572; A61B 5/150755; A61B 10/007; B01L 3/50; B01L 3/502; B01L 3/508; B01L 3/523; B01L 2200/026; B01L 2300/044; B01L 2400/049; B01L 3/563; G01N 33/49; G01N 33/493
See application file for complete search history.

(56) References Cited

U.S. PATENT DOCUMENTS

| 4,300,404 | A | 11/1981 | Mehl et al. |
| 4,852,560 | A | 8/1989 | Hermann, Jr. et al. |
| 4,927,605 | A * | 5/1990 | Dorn ............... A61B 10/007 422/68.1 |
| 5,254,314 | A * | 10/1993 | Yu ................... B01L 3/5457 422/918 |
| 5,312,009 | A * | 5/1994 | Ratajczak ....... A61B 10/0045 73/863.52 |
| 6,680,027 | B2 | 1/2004 | Kang |
| 2003/0053938 | A1* | 3/2003 | Szeles ............. A61B 10/007 600/583 |
| 2005/0032239 | A1* | 2/2005 | Katz ................ A61B 10/007 422/400 |
| 2009/0005704 | A1 | 1/2009 | Porat et al. |
| 2012/0043328 | A1* | 2/2012 | Pirner .............. B01L 3/50825 220/834 |
| 2013/0175266 | A1* | 7/2013 | Ellis ................. B01L 3/502 220/23.87 |
| 2018/0280002 | A1 | 2/2018 | Kopoian |

(Continued)

FOREIGN PATENT DOCUMENTS

WO WO-2011073729 A1 * 6/2011 ......... A61B 10/0096

*Primary Examiner* — Jill A Warden
*Assistant Examiner* — Dwayne K Handy
(74) *Attorney, Agent, or Firm* — Michael C. Balaguy

(57) ABSTRACT

A specimen cap. The specimen cap allows material to be transferred out of a specimen cup without exposing the user (clinician, lab tech, phlebotomist) to the sample. The cap employs a double cap system with a secondary cap providing access to a needle holder that holds a needle assembly. The needle assembly has an upward extending needle, with an optional needle cover, and a downward extending draw or sample tube extending downward to reach the sample contained in the specimen cup.

14 Claims, 5 Drawing Sheets

(56) References Cited

U.S. PATENT DOCUMENTS

2018/0103936 A1* 4/2018 Lei .......................... B01L 3/508
2018/0325497 A1* 11/2018 Katz .................... A61B 10/007
2019/0142394 A1   5/2019 Klaassen

* cited by examiner

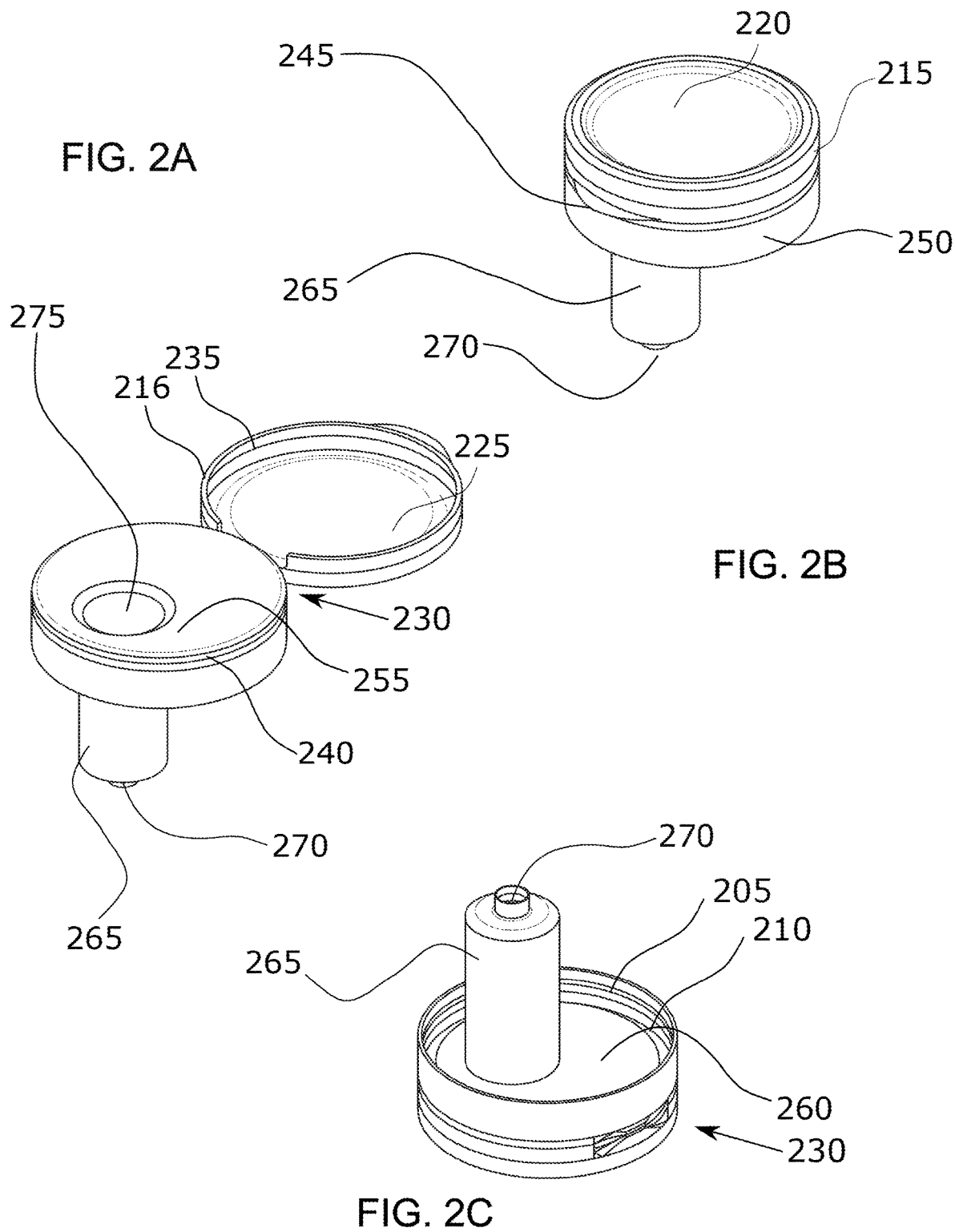

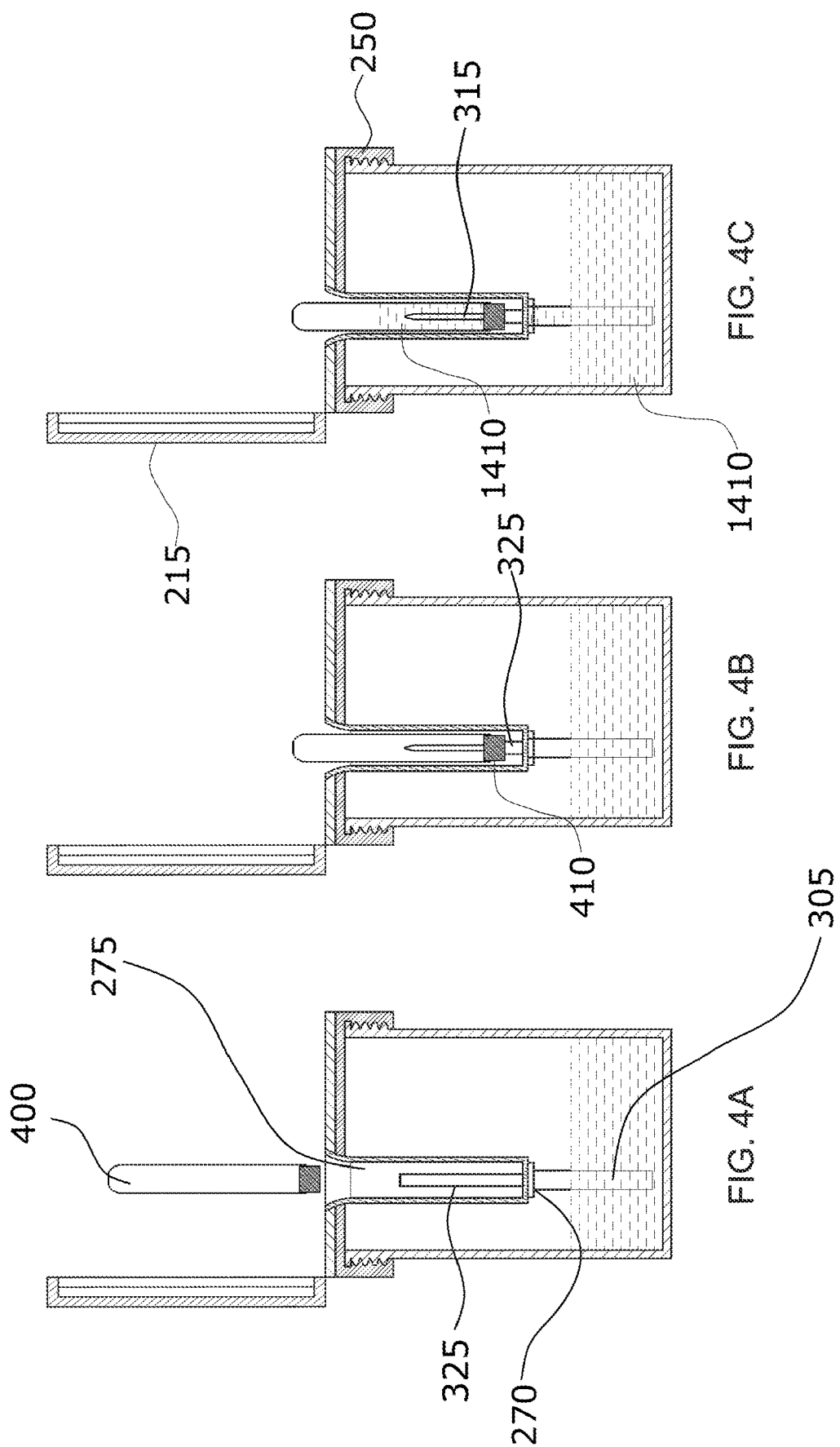

NEEDLECUP

BACKGROUND

The following includes information that may be useful in understanding the present disclosure. It is not an admission that any of the provided information is prior art or material to the presently described or claimed inventions or that any publication or document specifically or implicitly referenced is prior art.

Liquid specimens are usually collected in plastic or glass containers with a lid or cover to close the container. The specimens are then sent to a distant lab for analysis or put aside until a technician is ready to initiate the analysis procedure. At the lab or testing site, portions of the sample are transferred from the collection container to other containers more suitable for analyzing and storing the sample, such as test tubes. The specimens are often split into several aliquots to run different tests. For example, one aliquot may be tested for the presence of specific chemicals, enzymes, etc. and another may be tested for microorganism count or bacterial identity. Transferring the sample from the collection container under sterile conditions may risk exposing the technician to the specimen.

Not following proper techniques often harms the original sample's microbiological and chemical integrity as it is subjected to methods such as pouring, pipetting, and funneling it into a test tube or other receptacle. Additionally, the increased possibility of mislabeling occurs with each transfer may lead to erroneous results for a particular patient.

Proper use of a medical specimen collection cup, such as for a urine sample, requires protecting the specimen from contamination. Furthermore, it is often necessary to prevent the patient from becoming injured while using specialized collection cups.

The cup's open end portion and the cap's interior surfaces are particularly vulnerable to hand and body contact or the like before, during, and after the specimen collection. This contact can contaminate the specimen or cause injury. Conventional specimen cups do not shield these vulnerable areas from such contaminating contact or personal injury in a simple manner. Thus, a suitable solution is desired.

Various attempts have been made to solve problems found in specimen collection art: U.S. Patent and Publication Nos. 2019/0142394; 2009/0005704; U.S. Pat. Nos. 4,300,404; 4,852,560; 6,680,027 and 2018/0280002. This prior art is representative of specimen collection.

SUMMARY

Given the disadvantages inherent in the known art, this disclosure provides a novel specimen cap. One general aspect includes sample transfer without exposing the handler to the specimen in the cup.

The disclosed needle lid and optional specimen cup provide a system for removing samples from a specimen cup without exposing a clinician to any specimen's biological danger. The lid had a lower cover and an upper cover. The lower cover has a needle holder extending downward and a needle assembly extending downward enough into the specimen cup to reach beneath the sample's surface. Thus, suction on the needle assembly will draw samples out of the specimen cup. The collection tube supplies the vacuum in versions configured for use with an evacuated collection tube. The sample flows into the collection tube without releasing it into the environment or outside of the system. This containment allows safer handling by the clinician. In some versions, the upper cover is tightly capped to prevent or alleviate the danger of sample spillage from the specimen cup.

Some system versions are designed for use with a standard medical specimen cup, such as a urinalysis specimen cup. Some of these specimen cups have threaded rims for connecting to a lid. Some versions of the needle lid use a separate seal between the lid and the specimen cup, and these or other versions use an adhesive between the lid and the specimen cup.

In use, a sample is placed into the specimen cup, such as is typically accomplished for a urinalysis. The cup is capped with a needle lid and transported to a testing area. There, the clinician opens the upper cover, which allows access to the needle holder. When an evacuated collection tube is placed into the needle holder, the needle pierces the septum, and the vacuum in the collection tube draws a sample into the collection tube without exposing the clinician to the sample. Alternatively, the specimen cup could be capped with a standard lid when the sample is collected. When the sample reaches the testing area, the standard lid is carefully replaced with a needle lid, allowing subsequent handling without exposure to the sample.

In summarizing this device, certain aspects and advantages have been described. The new device or method may be made or carried out to achieve or optimize one set of advantages without necessarily achieving other advantages.

BRIEF DESCRIPTION OF THE DRAWINGS

The figures that accompany the written portion of this specification illustrate variations and methods of use for the present devices.

FIG. 2A is a perspective view of a specimen cup lid.

FIG. 2B is a perspective view of the lid of FIG. 2A in an alternative configuration.

FIG. 2C is a perspective view of the bottom of the lid of FIG. 2A.

FIG. 4A is a cross-section of a specimen cup lid.

FIG. 4B is a cross-section of a specimen cup lid in an "in-use" arrangement.

FIG. 4C is a cross-section of a specimen cup lid in an "in-use" arrangement after the needle has punctured the septum.

DETAILED DESCRIPTION

Figure 1:
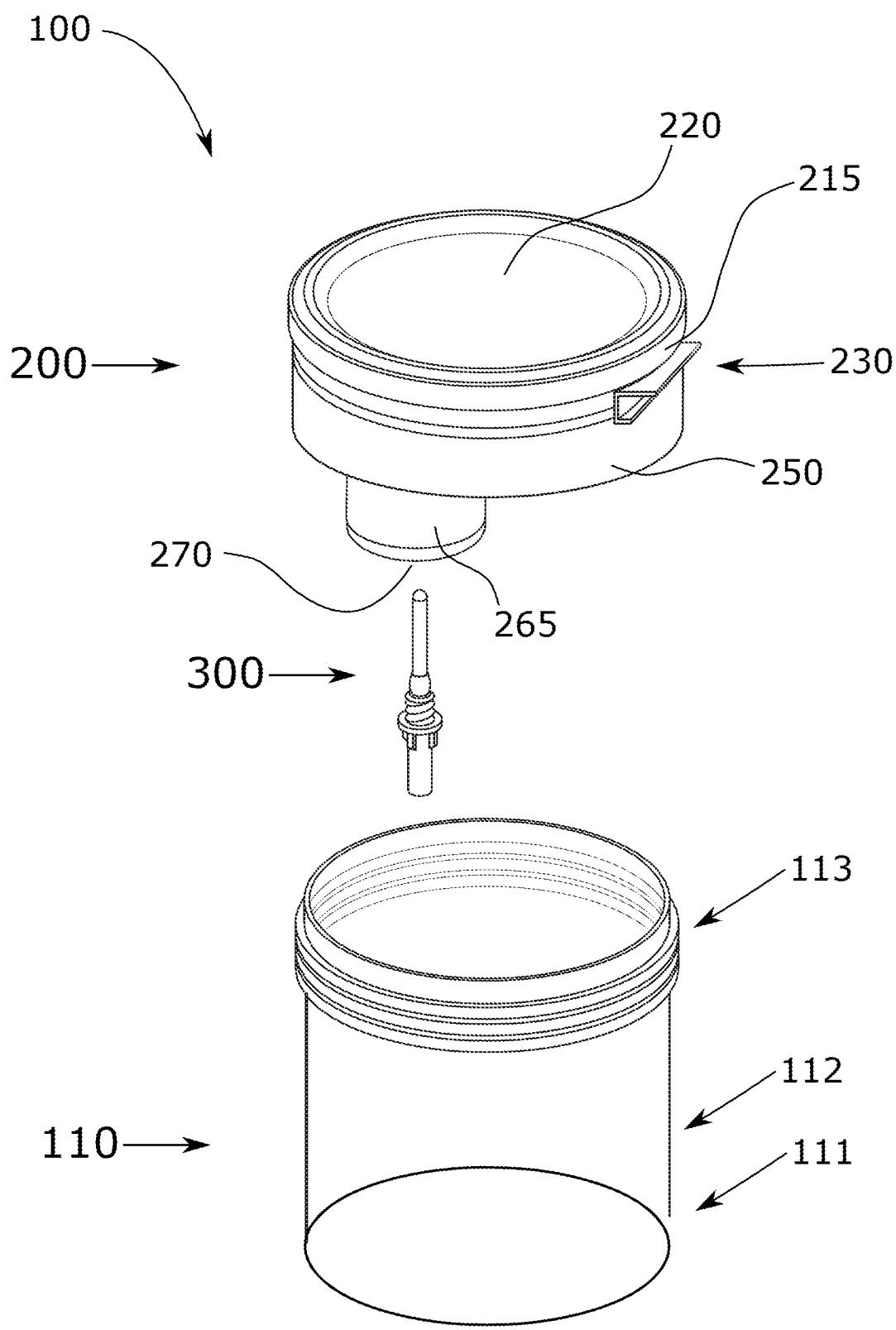
FIG. 1 is a perspective view of a specimen cup lid.

| | |
|---|---|
| needlecup | 100 |
| cup | 110 |
| base | 111 |
| walls | 112 |
| external threads | 113 |
| lid | 200 |
| internal threads | 205 |
| liquid seal | 210 |
| upper cover | 215 |
| upper cover walls | 216 |
| upper cover top | 220 |
| upper cover bottom | 225 |
| hinge | 230 |
| internal snaplock ridges | 235 |

| DETAILED DESCRIPTION | |
| --- | --- |
| external snaplock ridges | 240 |
| tab | 245 |
| lower cover | 250 |
| lower cover top | 255 |
| lower cover bottom | 260 |
| needle holder | 265 |
| threaded aperture | 270 |
| opening | 275 |
| needle assembly | 300 |
| sample inlet | 305 |
| needle hub | 310 |
| needle | 315 |
| needle cover | 320 |
| sample | 1410 |

Unless defined otherwise, all technical and scientific terms used in this document have the same meanings as commonly understood by one skilled in the art to which the disclosed invention pertains. Singular forms—a, an, and the—include plural referents unless the context indicates otherwise. Thus, a reference to "fluid" refers to one or more fluids, such as two or more fluids, three or more fluids, etc. When an aspect is said to include a list of components, the list is representative. If the component choice is specifically limited to the list, the disclosure will say so. Moreover, listing components acknowledges that exemplars exist for each component and any combination of the components—including combinations that exclude any one or any combination of the listed components. For example, "component A is chosen from A, B, or C" discloses exemplars with A, B, C, AB, AC, BC, and ABC. It also discloses (AB but not C), (AC but not B), and (BC but not A) as exemplars, for example. Combinations that one of ordinary skill in the art knows to be incompatible with each other or with the components' function in this device are excluded from this device, in some exemplars.

When an element or layer is referred to as being "on", "engaged to", "connected to" or "coupled to" another element or layer, it may be directly on, engaged, connected, or coupled to the other element or layer, or intervening elements or layers may be present. In contrast, when an element is referred to as being "directly on", "directly engaged to", "directly connected to", or "directly coupled to" another element or layer, there may be no intervening elements or layers present. Other words used to describe the relationship between elements should be interpreted in a like fashion (e.g., "between" versus "directly between", "adjacent" versus "directly adjacent", etc.).

Although the terms first, second, third, etc. may describe various elements, components, regions, layers, or sections, these elements, components, regions, layers, or sections should not be limited by these terms. These terms may only distinguish one element, component, region, layer, or section from another region, layer, or section. Terms such as "first", "second", and other numerical terms do not imply a sequence or order unless indicated by the context. Thus, a first element, component, region, layer, or section discussed below could be termed a second element, component, region, layer, or section without departing from this disclosure.

Spatially relative terms, such as "inner", "outer", "beneath", "below", "lower", "above", "upper" and the like, may be used for ease of description to describe one element or feature's relationship to another element or feature as illustrated in the figures. Spatially relative terms may be intended to encompass different orientations of the device in use or operation and the orientation depicted in the figures. For example, if the device in the figures is turned over, elements described as "below", or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors interpreted accordingly.

The description of the exemplars has been provided for purposes of illustration and description. It is not intended to be exhaustive or to limit the invention. Individual elements or features of a particular exemplar are generally not limited to that exemplar but, where applicable, are interchangeable and can be used in a selected exemplar, even if not explicitly shown or described. The same may also be varied in many ways. Such variations are not a departure from the invention, and all such modifications are included within the invention's scope.

FIG. 1 depicts lid 200. Lid 200 is designed to replace lids of a typical specimen cup 110. Typical specimen cup 110 has a base 111, walls 112, and external threads 113.

Lid 200 comprises upper cover 215 and lower cover 250. Upper cover 215 connects to lower cover 250 through hinge 230. Lower cover 250 has needle holder 265 extending downward from lower cover bottom 260. The needle holder 265 comprises needle aperture 270, which receives needle assembly 300. FIG. 1 shows needle assembly 300 and, consequently, needle aperture 270 as comprising a threaded interaction. In other exemplars, the interaction between needle assembly 300 and needle aperture 270 uses any semipermanent interconnection. For example, the interaction between needle assembly 300 and needle aperture 270 may be a press-fit, interference fit, sliding fit, friction fit, etc.

FIG. 2A depicts lid 200. In this depiction, upper cover 215 is in a closed configuration with upper cover top 220 pointing upwards. FIG. 2A shows needle holder 265 with needle aperture 270, like the FIG. 1 depiction. Upper cover 215 also comprises tab 245. FIG. 2B depicts lid 200 in an upper-cover-open configuration. This configuration reveals upper cover bottom 225, lower cover 250, lower cover top 255, and opening 275. Upper cover bottom 225 comprises internal snaplock ridges 235, which sit along upper cover walls 216.

Hinge 230 connects upper cover 215 to lower cover 250, allowing upper cover 215 to move from the close configuration depicted in FIG. 2A to the open configuration depicted in FIG. 2B.

Lower cover 250 comprises external snaplock ridges 240. As with FIG. 2A, FIG. 2B depicts needle holder 265 (which likewise comprises needle aperture 270). External ridges 240 interact with internal ridges 235 the hold upper cover 215 firmly, but not necessarily permanently, closed.

FIG. 2C is a perspective view of lid 200. FIG. 2C reveals the bottom 260 of lower cover 250. FIG. 2C also reveals liquid seal 210 and internal threads 205. As before, needle holder 265 comprises needle aperture 270 extending up from lower cover bottom 260.

Figure 3A:
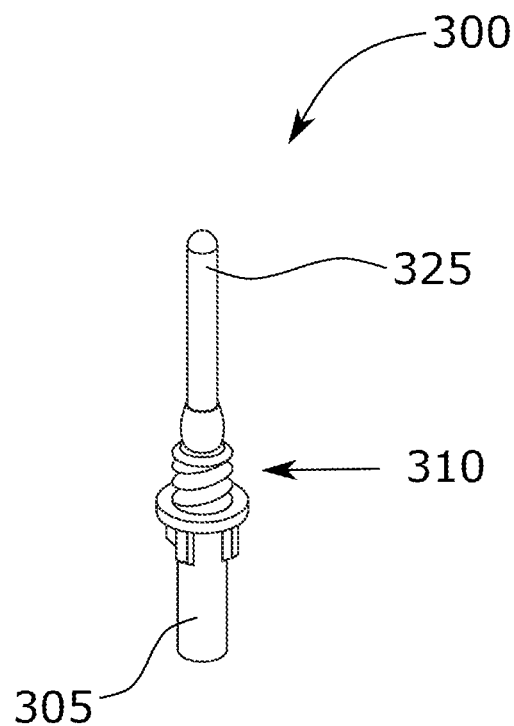
FIG. 3A is a perspective view of a component of the lid of FIG. 3A.

FIG. 3A depicts a perspective view of needle assembly 300. Needle assembly 300 comprises a sample inlet 305, which extends downward from needle hub 310. Needle 315 (see FIG. 3B) extends up from the needle hub 310 and in FIG. 3A, needle cover 325 is disposed over needle 315 and secured to needle hub 310. In some versions, needle assembly 300 is a modified version of a multisample needle such as those used in VACUTAINER or MONOJET blood collection systems.

Figure 3B:
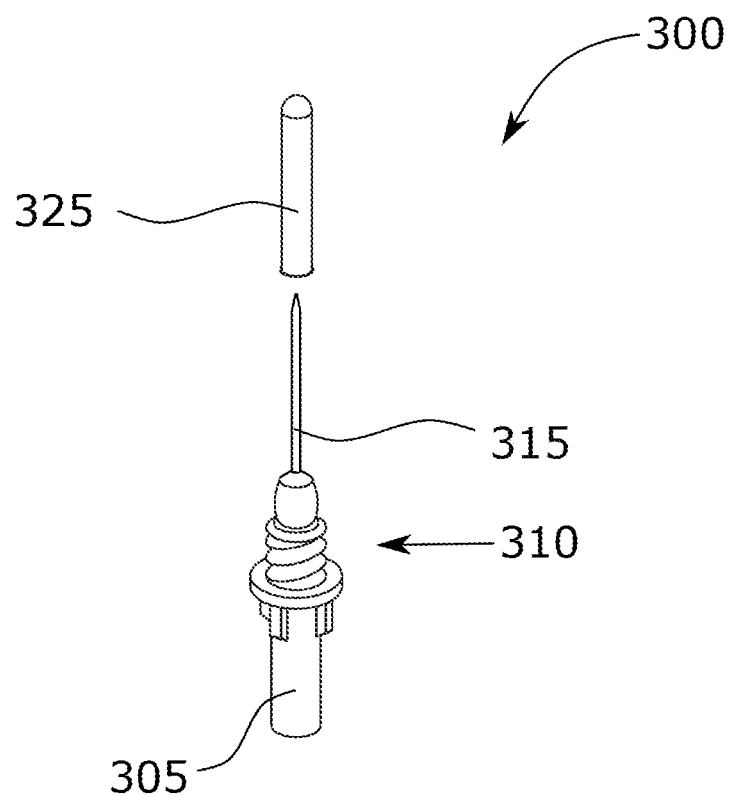
FIG. 3B is a perspective view of a component of FIG. 3A in an alternative configuration.

FIG. 3B shows the same view as shown in FIG. 3A, except that needle cover 325 is removed to reveal needle 315. When lid 200 is assembled, needle assembly 300 is secured into needle holder 265. The figures depict this connection as a threaded connection, but any connection that holds needle assembly 300 in place will function as a connection mechanism. The figures show needle assembly 300 extending up into needle holder 265. But other exemplars exist in which needle assembly 300 drops down into needle holder 265 through opening 275.

FIG. 4A depicts a cross-section of cup 110 and lid 200 in an operational configuration.

The dotted lines indicate sample 1410. As can be seen in FIG. 4A, sample inlet 305 extends below the level of sample 1410.

FIG. 4B shows an evacuated collection tube 400 partially mated with needle cup 100 with septum 410 positioned above and pointing toward needle 315 and needle cover 325. FIG. 4C shows collection tube 400 after needle 315 has punctured septum 410, and some of sample 1410 has entered collection tube 400.

Figure 5:
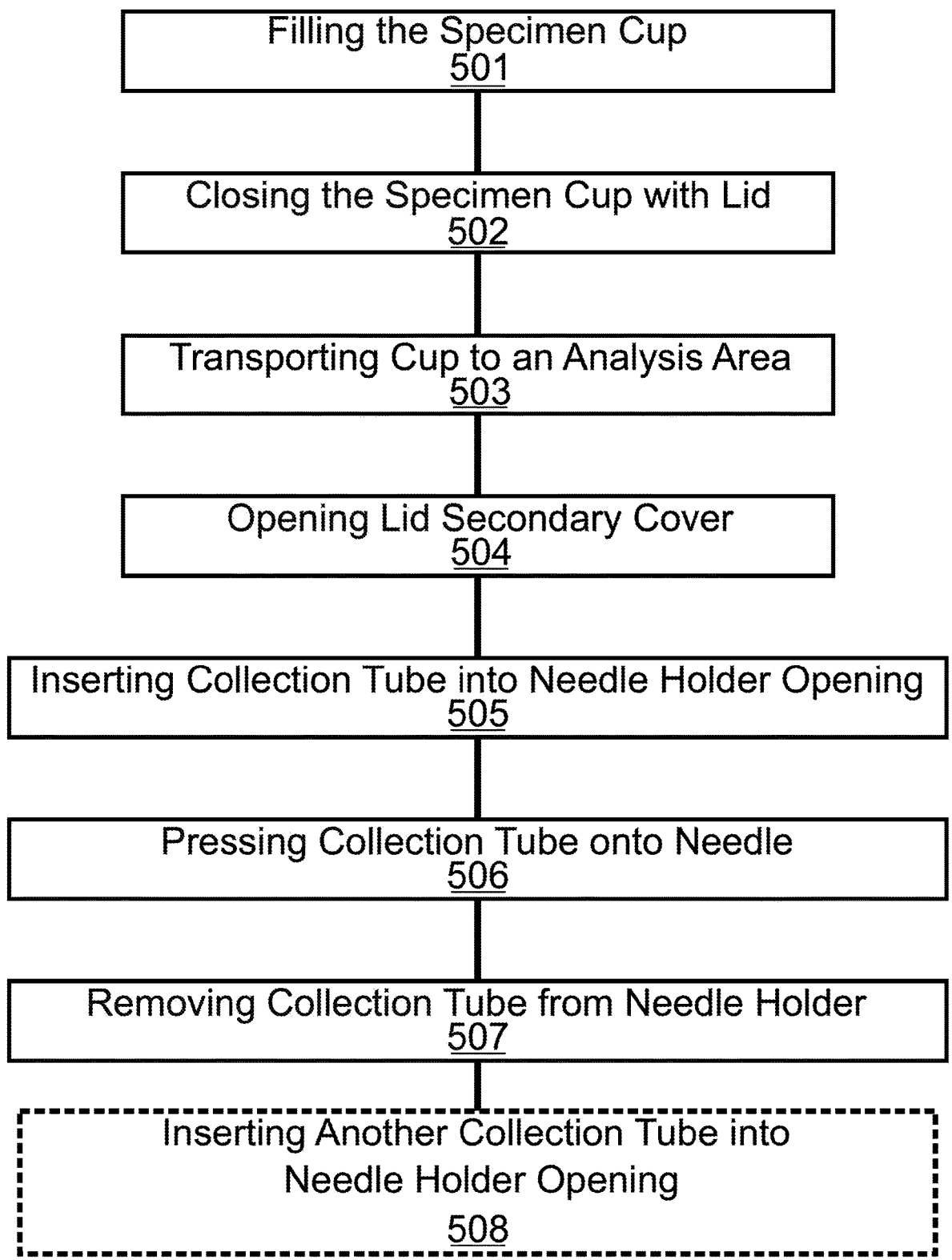
FIG. 5 is a flow chart representing a method of using a specimen cup lid.

FIG. 5 depicts a method of using lid 200. Step 501 comprises filling cup 110 with sample 1410. Step 502 comprises closing cup 110 with lid 200. In some exemplars of lid 200, those with an adhesive, step 502 also comprises gluing lid 200 to cup 110.

Step 503 comprises transporting cup 110 to an analysis area. Step 504 comprises opening upper cover 215. In some exemplars, tab 245 facilitates opening upper cover 215. In these or other exemplars, opening upper cover 215 comprises overcoming the holding force applied by the interaction between internal snaplock ridges 235 and external snaplock ridges 240. Opening upper cover 215 occurs without any release of the sample. And opening upper cover 215 exposes lower cover 250 and opening 275.

Step 505 comprises inserting an evacuated collection tube 400, septum down, into opening 275 inside needle holder 265.

Step 506 comprises pressing collection tube 400 onto needle 315, causing needle 315 to pierce needle cover 325 and septum 410. Once needle 315 pierces septum 410, the vacuum inside of collection tube 400 transfers sample 1410 into collection tube 400. In some exemplars, this transfer occurs without any spillage of sample 1410.

Step 507 comprises removing collection tube 400 from needle holder 265.

Optional step 508 comprises inserting another instance of collection tube 400 into opening 275, pressing collection tube 400 over needle cover 325 and septum 410, and transferring another aliquot of sample 1410 into the second instance of collection tube 400.

The components of lid 200 are constructed from typical materials. For example, a plastic material, as is well known in the art, is suitable for the upper cover 215, lower cover 250, hinge 230, and needle hub 310. Stainless steel is suitable for needle 315. Flexible plastic or rubber is suitable for needle cover 325. Some exemplars supply lid 200 without cup 110, and other exemplars supply lid 200 and cup 110 together.

While particular exemplars of the present invention have been shown and described, it will be obvious to those skilled in the art that changes and modifications can be made without departing from the exemplars of this invention in its broader aspects and, therefore, the appended claims are to encompass within their scope all such changes and modifications as fall within the true, intended, explained, disclose, and understood scope and spirit of this invention's many exemplars and alternative descriptions.

Additionally, various exemplars have been described above. For convenience's sake, combinations of aspects composing invention exemplars have been listed so that one of ordinary skill in the art may read them exclusive of each other when they are not necessarily intended to be exclusive. But a recitation of an aspect for one exemplar is meant to disclose its use in all exemplars in which that aspect can be incorporated without undue experimentation. Likewise, a recitation of an aspect as composing part of an exemplar is a tacit recognition that a supplementary exemplar excludes that aspect explicitly. All patents, test procedures, and other documents cited in this specification are fully incorporated by reference to the extent that this material is consistent with this specification and for all jurisdictions in which such incorporation is permitted.

Moreover, some exemplars recite ranges. When this is done, it is meant to disclose the ranges as a range and disclose each point within the range, including endpoints. For those exemplars that disclose a specific value or condition for an aspect, supplementary exemplars exist that are otherwise identical but that specifically exclude the value or the conditions for the aspect.

What is claimed is:

1. A lid comprising:
   an upper cover;
   a lower cover below the upper cover, having a bottom with a needle holder extending downward from the bottom;
   and
   a needle assembly disposed in the needle holder,
   wherein the upper cover connects to the lower cover with a hinge located on an edge of the lower cover;
   wherein the needle assembly comprises a downward extending blunt sample inlet;
   wherein the needle assembly further comprises an upward extending needle;
   wherein the needle assembly further comprises a needle cover;
   wherein the upper cover further comprises internal snaplock ridges; and
   wherein the lower cover further comprises external snaplock ridges that interface with the internal snaplock ridges.

2. The lid of claim 1, wherein the lower cover has a recess for receiving a specimen cup and forming a liquid tight connection, and the connection is liquid tight.

3. The lid of claim 2, wherein the connection between the specimen cup and the lid is threaded.

4. The lid of claim 3, wherein the lid further comprises a seal, an adhesive, or both disposed between a lid edge and a specimen cup edge.

5. The lid of claim 4, wherein the needle is connected with a threaded, leak-tight connection.

6. The lid of claim 5, wherein the sample inlet extends toward the specimen cup's bottom.

7. The lid of claim 6, wherein the sample inlet extends downward to within 5, 4, 3, 2, or 1 mm of the specimen cup's bottom.

8. The lid of claim 7, wherein the sample inlet has a diameter greater than the needle's diameter.

9. A method of retrieving a sample comprising: providing a specimen cup having a sample, wherein the specimen cup is capped with the lid of claim 1;
   retrieving the sample through the lid.

10. The method of claim 9 further comprising testing the sample without exposing a user to the sample.

11. The method of claim 10, wherein the retrieving step comprises transferring part of the sample into an evacuated collection tube using the needle assembly.

12. The method of claim 11, wherein transferring comprises transferring the sample without spillage.

13. The lid of claim 1, wherein the upper cover further comprises a skirt, and the internal snaplock ridges are disposed interior to the skirt, and the skirt circumscribes the external snaplock ridges of the lower cover when the upper cover is closed to the lower cover.

14. The lid of claim 1, wherein each of the external snaplock ridges are annular, and each of the internal snaplock ridges are annular.

\* \* \* \* \*